US012736449B2

(12) United States Patent
Kim et al.

(10) Patent No.: US 12,736,449 B2
(45) Date of Patent: Sep. 15, 2026

(54) APPARATUS FOR INSPECTING FATIGUE FRACTURE OF HOUSING WELDING PART OF BATTERY MODULE

(71) Applicant: LG ENERGY SOLUTION, LTD., Seoul (KR)

(72) Inventors: Dong-Wook Kim, Daejeon (KR); Yong-Il Kim, Daejeon (KR); Su-Hang Lee, Daejeon (KR)

(73) Assignee: LG ENERGY SOLUTION, LTD., Seoul (KR)

( * ) Notice: Subject to any disclaimer, the term of this patent is extended or adjusted under 35 U.S.C. 154(b) by 355 days.

(21) Appl. No.: 18/031,423

(22) PCT Filed: Nov. 9, 2021

(86) PCT No.: PCT/KR2021/016282
§ 371 (c)(1),
(2) Date: Apr. 12, 2023

(87) PCT Pub. No.: WO2022/103132
PCT Pub. Date: May 19, 2022

(65) Prior Publication Data

US 2023/0375449 A1 Nov. 23, 2023

(30) Foreign Application Priority Data

Nov. 10, 2020 (KR) ........................ 10-2020-0149662

(51) Int. Cl.
*G01N 3/10* (2006.01)
*H01M 10/42* (2006.01)
(Continued)

(52) U.S. Cl.
CPC .......... *G01N 3/10* (2013.01); *H01M 10/4285* (2013.01); *G01M 5/0033* (2013.01);
(Continued)

(58) Field of Classification Search
CPC ............. G01N 3/10; G01N 2203/0067; G01N 2203/0073; G01N 2203/0296;
(Continued)

(56) References Cited

U.S. PATENT DOCUMENTS 10,193,181 B2 * 1/2019 Niwa .................. H01M 50/291
2011/0123882 A1 * 5/2011 Kim ...................... H01M 8/248
429/428
(Continued)

FOREIGN PATENT DOCUMENTS

CN 201853812 U 11/2010
CN 204255553 U 4/2015
(Continued)

OTHER PUBLICATIONS

Extended European Search Report for European Application No. 21892299.5, dated Nov. 22, 2023.
(Continued)

*Primary Examiner* — Jonathan M Dunlap
(74) *Attorney, Agent, or Firm* — Birch, Stewart, Kolasch & Birch, LLP

(57) ABSTRACT

Discussed is a fatigue failure verification device that can include a module housing including a welding portion, a cell stack including a plurality of battery cells accommodated in the module housing, at least one main flexible tube located in a central portion of the cell stack in a stack direction of the cell stack, a main flexible tube frame in which the at least one main flexible tube is accommodated. The main flexible tube frame can include a pair of opening portions formed on opposite sides so that the at least one main flexible tube faces the plurality of battery cells, and a pump can be provided, which is configured to adjust a pressure applied by the at least one main flexible tube to the plurality of battery cells by supplying a fluid to the at least one main flexible tube.

15 Claims, 10 Drawing Sheets

(51) Int. Cl.
*G01M 5/00* (2006.01)
*G01N 33/00* (2006.01)

(52) U.S. Cl.
CPC ..... *G01N 33/0078* (2024.05); *G01N 33/0095* (2024.05); *G01N 2203/0067* (2013.01); *G01N 2203/0073* (2013.01); *G01N 2203/0296* (2013.01)

(58) Field of Classification Search
CPC .......... G01N 33/0078; G01N 33/0095; G01M 5/0033; H01M 10/4285; Y02E 60/10
See application file for complete search history.

(56) References Cited

U.S. PATENT DOCUMENTS

| | | | | |
|---|---|---|---|---|
| 2015/0020578 | A1 | 1/2015 | Kim et al. | |
| 2016/0064972 | A1 | 3/2016 | Stefanopoulou et al. | |
| 2016/0308186 | A1 | 10/2016 | Han | |
| 2017/0133705 | A1* | 5/2017 | Niwa | H01M 50/291 |
| 2017/0279088 | A1* | 9/2017 | Reinshagen | H01M 50/264 |
| 2018/0062127 | A1 | 3/2018 | Lee et al. | |
| 2019/0006699 | A1* | 1/2019 | Jones | H01M 10/6563 |
| 2020/0044293 | A1 | 2/2020 | Choi et al. | |
| 2020/0168959 | A1 | 5/2020 | Hettrich | |
| 2021/0197691 | A1 | 7/2021 | Stefanopoulou et al. | |
| 2022/0393284 | A1* | 12/2022 | Kim | H01M 10/6567 |

FOREIGN PATENT DOCUMENTS

| | | | | | |
|---|---|---|---|---|---|
| CN | 106133944 | A | | 11/2016 | |
| CN | 110311068 | A | | 10/2019 | |
| EP | 3886202 | A1 | * | 9/2021 | H01M 10/44 |
| JP | 2006-202560 | A | | 8/2006 | |
| JP | 2010-238554 | A | | 10/2010 | |
| JP | 2012-64508 | A | | 3/2012 | |
| JP | 2012-114030 | A | | 6/2012 | |
| JP | 2012221773 | A | * | 11/2012 | |
| JP | 5444762 | B2 | | 3/2014 | |
| JP | 2015-133180 | A | | 7/2015 | |
| JP | 2015-161514 | A | | 9/2016 | |
| JP | 2018-106930 | A | | 7/2018 | |
| JP | 2018-116914 | A | | 7/2018 | |
| JP | 2020-20242 | A | | 2/2020 | |
| KR | 10-2011-0048091 | A | | 5/2011 | |
| KR | 10-1198857 | B1 | | 11/2012 | |
| KR | 10-2015-0009876 | A | | 1/2015 | |
| KR | 10-2018-0099668 | A | | 9/2018 | |
| KR | 10-2018-0136192 | A | | 12/2018 | |
| KR | 10-2019-0142513 | A | | 12/2019 | |
| KR | 10-2146075 | B1 | | 8/2020 | |
| KR | 20230083578 | A | * | 6/2023 | G01L 17/00 |

OTHER PUBLICATIONS

International Search Report (PCT/ISA/210) issued in PCT/KR2021/016282, dated Feb. 22, 2022.

* cited by examiner

APPARATUS FOR INSPECTING FATIGUE FRACTURE OF HOUSING WELDING PART OF BATTERY MODULE

TECHNICAL FIELD

The present disclosure relates to a fatigue failure verification device for a housing welding portion of a battery module, and more particularly, to a fatigue failure verification device configured to implement a phenomenon in which repeated fatigue accumulates in a housing according to swelling of battery cells accommodated in the housing in a battery module as close to reality as possible.

The present application claims priority to Korean Patent Application No. 10-2020-0149662 filed on Nov. 10, 2020 in the Republic of Korea, the disclosures of which are incorporated herein by reference.

BACKGROUND ART

As charging and discharging of a battery module is repeated and expansion and contraction of a battery cell due to swelling of the battery cell repeatedly occurs, fatigue may accumulate in a welding portion of a housing in which the battery cell is accommodated, resulting in damage to the housing. In order to prevent damage to the welding portion, a material, a thickness, a depth, etc. of the welding portion between plates constituting the housing should be designed by considering the swelling of the battery cell. However, because a fatigue test through charging and discharging takes a lot of time, there is a need to develop a verification device capable of providing conditions similar to actual conditions.

Referring to FIG. 1, a conventional welding portion fatigue failure verification device is illustrated. The conventional welding portion fatigue failure verification device has a structure in which a battery cell 2 and a buffer pad 3 are located inside a housing 1 and a small hydraulic unit 4 is located in a central portion of a battery cell stack.

The conventional welding portion fatigue failure verification device having the structure may partially help to design a housing welding portion through simulation of whether a welding portion 1*a* is damaged by reproducing fatigue accumulation due to repeated expansion and contraction of the battery cell 2 in a plane direction.

However, the conventional welding portion fatigue failure verification device having the structure has problems in that it is difficult to apply a uniform force to the entire area of the battery cell and in particular, when a size of a battery module is small, it is difficult to apply a sufficient force because only a very small hydraulic unit may be installed.

Accordingly, there is a need to develop a welding portion fatigue failure verification device capable of providing an environment similar to an actual swelling environment in a battery module, when compared to the conventional welding portion fatigue failure verification device.

DISCLOSURE

Technical Problem

The present disclosure is designed to solve the problems of the related art, and therefore the present disclosure is directed to appropriately designing a welding portion of a module housing by providing an environment similar to an actual swelling environment in a battery module.

However, the technical purpose to be solved by the present disclosure is not limited to the above, and other objects not mentioned herein will be clearly understood by one of ordinary skill in the art from the following disclosure.

Technical Solution

In one aspect of the present disclosure, there is provided a fatigue failure verification device including: a module housing including a welding portion; a cell stack including a plurality of battery cells accommodated in the module housing; at least one main flexible tube located in a central portion of the cell stack in a stack direction of the cell stack; a main flexible tube frame in which the at least one main flexible tube is accommodated, the main flexible tube frame including a pair of opening portions formed on opposite sides so that the at least one main flexible tube faces the plurality of battery cells; and a pump configured to adjust a pressure applied by the at least one main flexible tube to the plurality of battery cells by supplying a fluid to the at least one main flexible tube.

The fatigue failure verification device may further include a pair of sub-flexible tubes respectively located between an upper plate of the module housing and the cell stack and between the upper plate of the module housing and the main flexible tube frame, and between a lower plate of the module housing and the cell stack and between the lower plate of the module housing and the main flexible tube frame.

The pump may be configured to individually control an amount of the fluid supplied to the at least one main flexible tube and the pair of sub-flexible tubes.

The fatigue failure verification device may be located between a pair of support walls, and wherein the fatigue failure verification device further includes a plurality of displacement sensors respectively located between a side of the module housing in a longitudinal direction of the module housing and one of the pair of support walls and between another side of the module housing in the longitudinal direction of the module housing and another of the pair of support walls.

The fatigue failure verification device may further include a pair of buffer pads respectively provided on opposite outermost sides of the cell stack in the stack direction of the cell stack.

A plurality of main flexible tubes may be provided, and the plurality of main flexible tubes are stacked in a width direction of the battery cell in the main flexible tube frame.

A plurality of main flexible tubes may be provided, wherein the plurality of main flexible tubes are stacked in a longitudinal direction of the plurality of battery cells in the main flexible tube frame.

A plurality of main flexible tubes may be provided, and the plurality of main flexible tubes are stacked in a width direction and a longitudinal direction of the plurality of battery cells in the main flexible tube frame.

The pump may be configured to individually control an amount of the fluid supplied to the plurality of main flexible tubes.

The fatigue failure verification device may further include a pair of sub-flexible tubes respectively located between an upper plate and a lower plate of the module housing and the cell stack, and between the upper plate and the lower plate of the module housing and the main flexible tube frame, wherein the pump is configured to individually control an amount of the fluid supplied to the plurality of main flexible tubes and the pair of sub-flexible tubes.

Advantageous Effects

According to an aspect of the present disclosure, a welding portion of a module housing may be appropriately designed by providing an environment similar to an actual swelling environment in a battery module.

DESCRIPTION OF DRAWINGS

The accompanying drawings illustrate a preferred embodiment of the present disclosure and together with the foregoing disclosure, serve to provide further understanding of the technical features of the present disclosure, and thus, the present disclosure is not construed as being limited to the drawing.

BEST MODE

Hereinafter, preferred embodiments of the present disclosure will be described in detail with reference to the accompanying drawings. Prior to the description, it should be understood that the terms used in the specification and the appended claims should not be construed as limited to general and dictionary meanings, but interpreted based on the meanings and concepts corresponding to technical aspects of the present disclosure on the basis of the principle that the inventor is allowed to define terms appropriately for the best explanation. Therefore, the description proposed herein is just a preferable example for the purpose of illustrations only, not intended to limit the scope of the disclosure, so it should be understood that other equivalents and modifications could be made thereto without departing from the scope of the disclosure.

Figure 1:
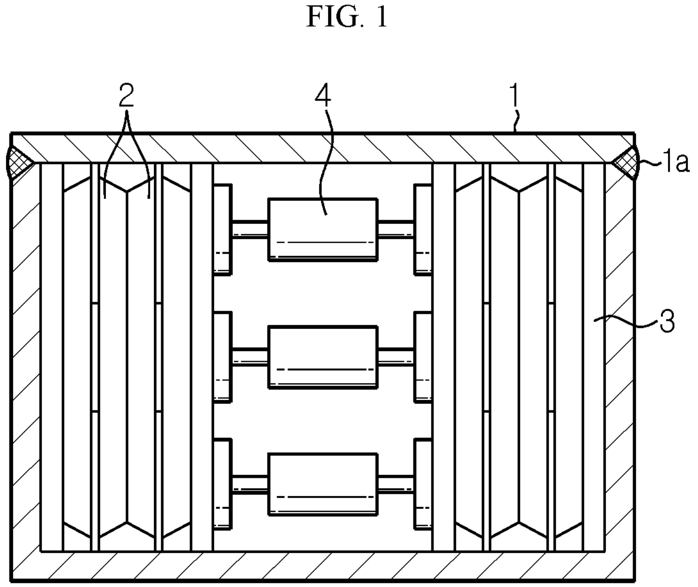
FIG. 1 is a view illustrating a conventional welding portion fatigue failure verification device.
Figure 2:
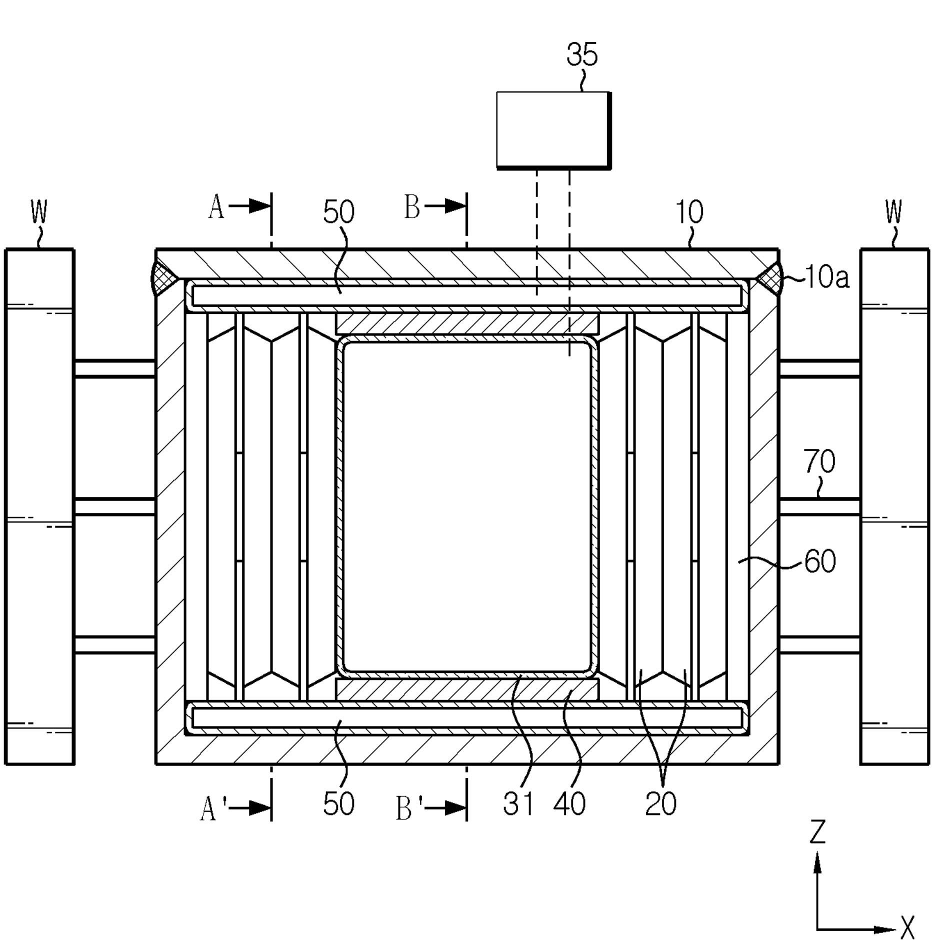
FIGS. 2 through 4 are views illustrating a fatigue failure verification device according to First Embodiment of the present disclosure.
Figure 3:
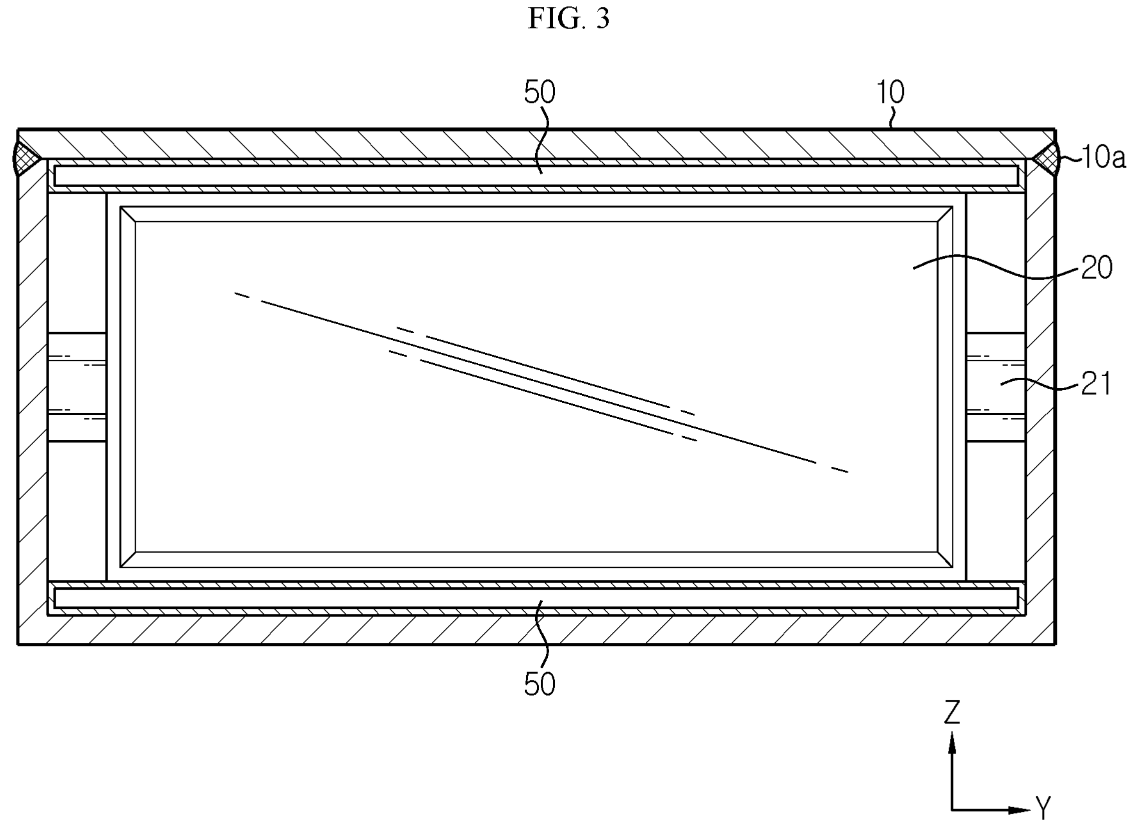
Figure 4:
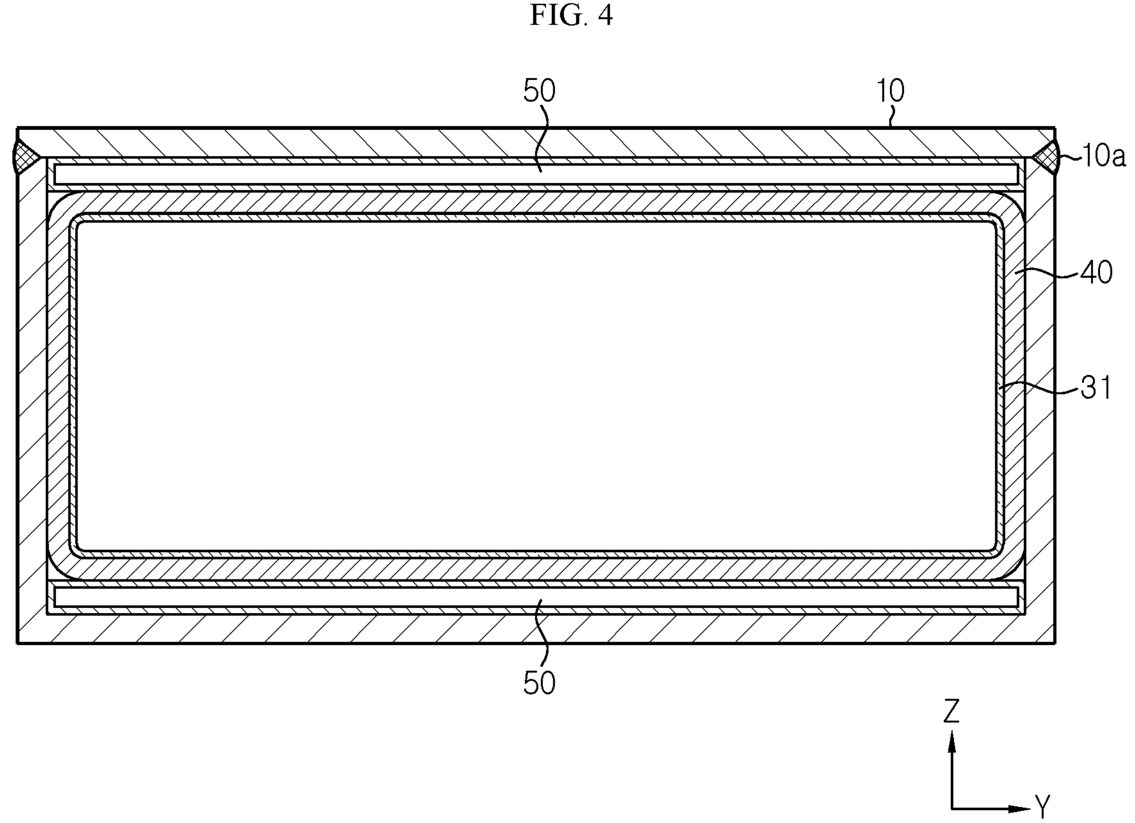

Referring to FIGS. 2 through 4, a fatigue failure verification device according to First Embodiment of the present disclosure includes a module housing 10, a cell stack including a plurality of battery cells 20, a main flexible tube 31, a pump 35, and a main flexible tube frame 40. The fatigue failure verification device may further include a pair of sub-flexible tubes 50 and/or a pair of buffer pads 60 and/or a plurality of displacement sensors 70, in addition to the above elements.

The module housing 10 may be formed by welding a plurality of plates, and thus, a welding portion 10*a* is formed on a part of the module housing 10.

The cell stack is accommodated in the module housing 10. The battery cells 20 constituting the cell stack may be, for example, pouch-type battery cells. The battery cell 20 extends in a width direction (direction parallel to a Y-axis) of the module housing 10 in the module housing 10.

That is, in the specification, a longitudinal direction (direction parallel to the Y-axis) of the battery cell 20 and the width direction (direction parallel to the Y-axis) of the housing 10 are the same direction. The battery cell 20 includes a pair of electrode leads 21 drawn out in the same direction or opposite directions in the longitudinal direction (direction parallel to the Y-axis) of the battery cell 20.

The main flexible tube 31 is located in a central portion of the cell stack in a stack direction (direction parallel to an X-axis) of the cell stack. That is, the main flexible tube 31 is located between the battery cells 20 located in the central portion from among the plurality of battery cells 20 constituting the cell stack. The main flexible tube 31 expands due to a fluid supplied from the pump 35, and thus, presses the battery cells 20 located on both sides of the main flexible tube 31 toward side walls of the module housing 10. The fatigue failure verification device according to First Embodiment of the present disclosure illustrated in FIGS. 2 through 4 includes one main flexible tube 31.

The pump 35 is provided outside the module housing 10, and adjusts a pressure applied by the main flexible tube 31 to the battery cell 20 by supplying a fluid to the main flexible tube 31.

As described below, the fatigue failure verification device according to the present disclosure may further include the pair of sub-flexible tubes 50 in addition to the main flexible tube 31. In this case, the pump 35 may individually adjust the amount of a fluid supplied to the main flexible tube 31 and the sub-flexible tubes 50.

Also, as described below, the fatigue failure verification device according to the present disclosure may include a plurality of main flexible tubes 32, 33, 34. In this case, the pump 35 may individually adjust the amount of a fluid supplied to the plurality of main flexible tubes 32, 33, 34. When the fatigue failure verification device according to the present disclosure includes the plurality of main flexible tubes 32, 33, 34 and also includes the pair of sub-flexible tubes 50, the pump 35 may individually adjust the amount of a fluid supplied to the plurality of main flexible tubes 32, 33, 34 and the pair of sub-flexible tubes 50.

The pump 35 may include a plurality of unit pumps which are physically separated from one another, in order to individually control the amount of a fluid supplied to the plurality of flexible tubes as described above.

The main flexible tube frame 40 accommodates the main flexible tube 31 in the module housing 10. The main flexible tube frame 40 includes a pair of opening portions formed on both sides so that the main flexible tube 31 faces the battery cell 20.

A volume expansion direction of the flexible tube frame 40 is limited so that the flexible tube frame 40 does not expand in a direction in which the opening portions are formed, that is, a direction other than the stack direction (direction parallel to the X-axis) of the cell stack. Due to the application of the flexible tube frame 40, the main flexible tube 31 presses the battery cell 20 facing the main flexible tube 31 only in the stack direction (direction parallel to the X-axis) of the cell stack. That is, the main flexible tube 31 corresponds to an element for generating a pressing force according to expansion of the battery cell 20 in a thickness direction (direction parallel to the X-axis) of the battery cell 20 occurring during swelling of the battery cell 20.

Unlike the main flexible tube 31, the sub-flexible tube 50 corresponds to an element for generating a pressing force according to expansion of the battery cell 20 in a width direction (direction parallel to a Z-axis) of the battery cell 20 occurring during swelling of the battery cell 20. In the cell stack including pouch-type battery cells, while volume expansion due to swelling mostly occurs in the stack direction, some volume expansion occurs in the width direction (direction parallel to the Z-axis) of the battery cell 20. In this regard, the fatigue failure verification device according to the present disclosure may include the sub-flexible tube 50.

A pair of sub-flexible tube 50 may be provided. One of the pair of sub-flexible tube 50 is located between an upper plate of the module housing 10 and the cell stack and between the upper plate of the module housing 10 and the main flexible tube frame 40. The other one of the pair of sub-flexible tube 50 is located between a lower plate of the module housing 10 and the cell stack and between the lower plate of the module housing 10 and the main flexible tube frame 40.

The pair of buffer pads 60 are respectively provided on both outermost sides of the cell stack in the stack direction (direction parallel to the X-axis) of the cell stack.

A plurality of displacement sensors 70 may be respectively provided on a side and the other side of the module housing 10 in a longitudinal direction of the module housing 10. The fatigue failure verification device may be located between a pair of support walls W. In this case, the plurality of displacement sensors 70 are respectively located between a side of the module housing 10 in the longitudinal direction of the module housing 10 and the support wall W and between the other side of the module housing 10 in the longitudinal direction of the module housing 10 and the support wall W.

When a pair of side walls located on both sides of the module housing 10 in the longitudinal direction (direction parallel to the X-axis) of the module housing 10 are deformed by a pressing force according to expansion of the main flexible tube 31, the displacement sensor 70 measures the amount of deformation.

Figure 5:
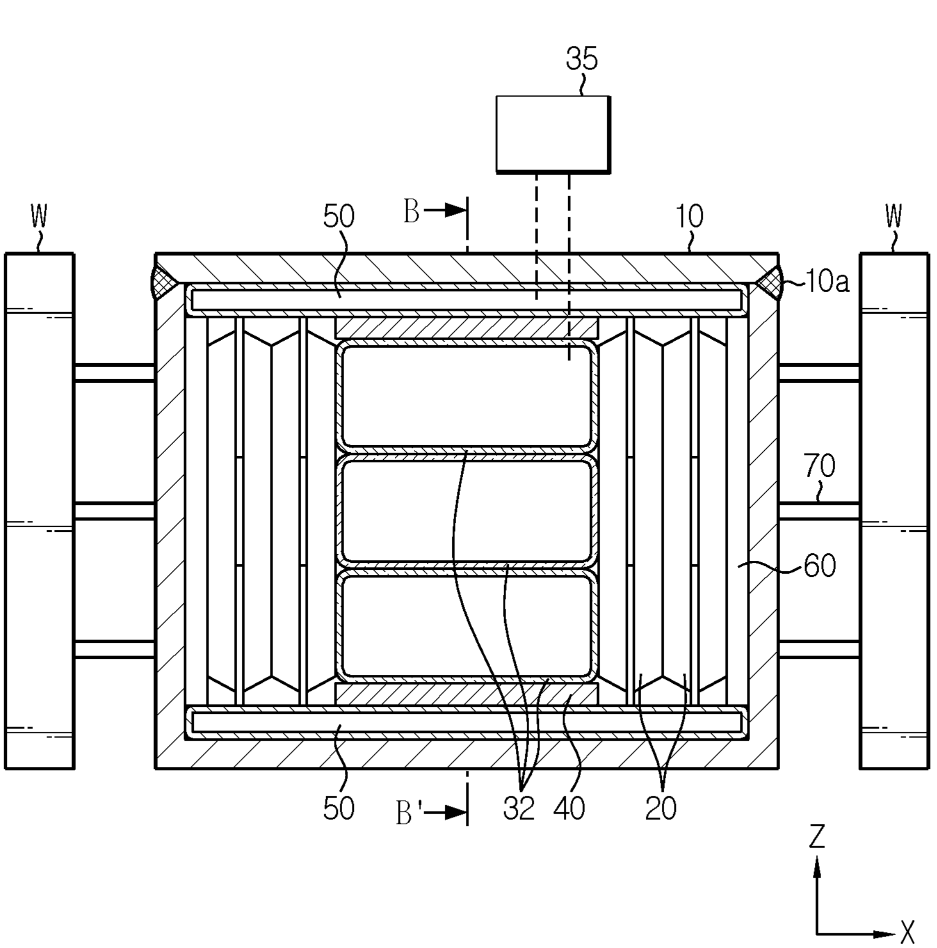
FIGS. 5 and 6 are views illustrating a fatigue failure verification device according to Second Embodiment of the present disclosure.
Figure 6:
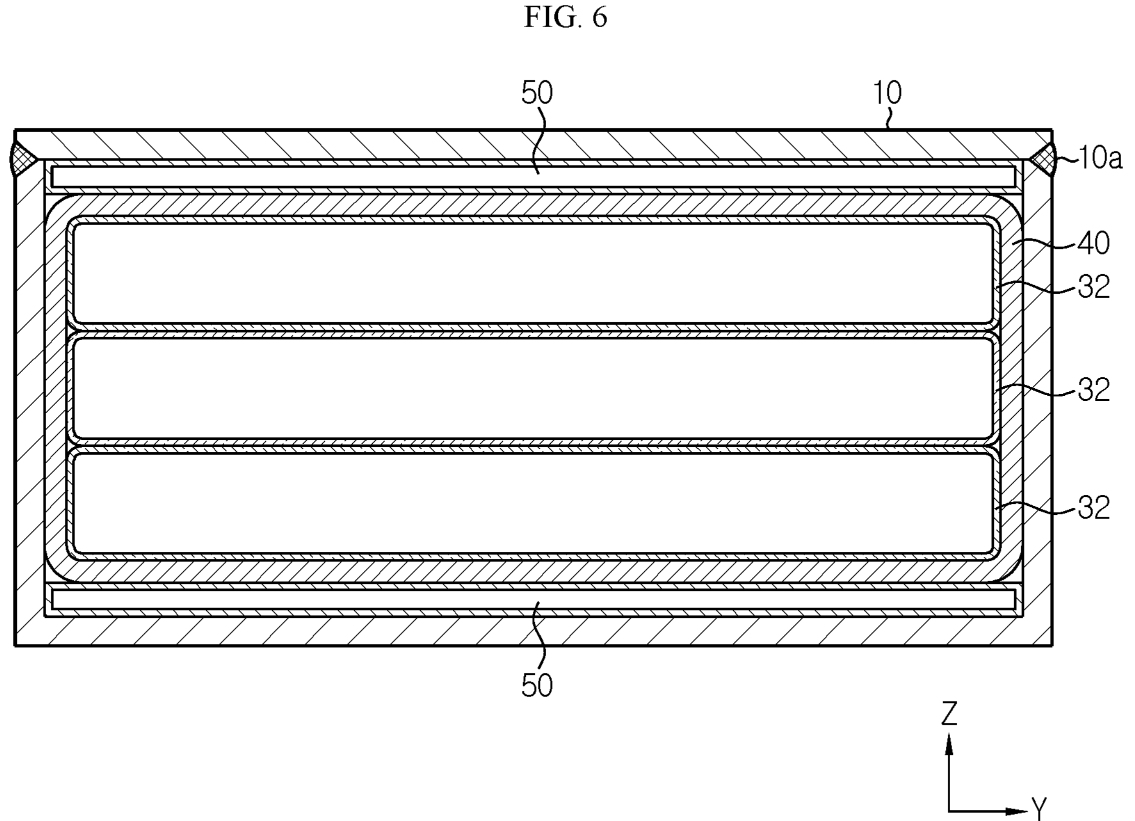
Figure 7:
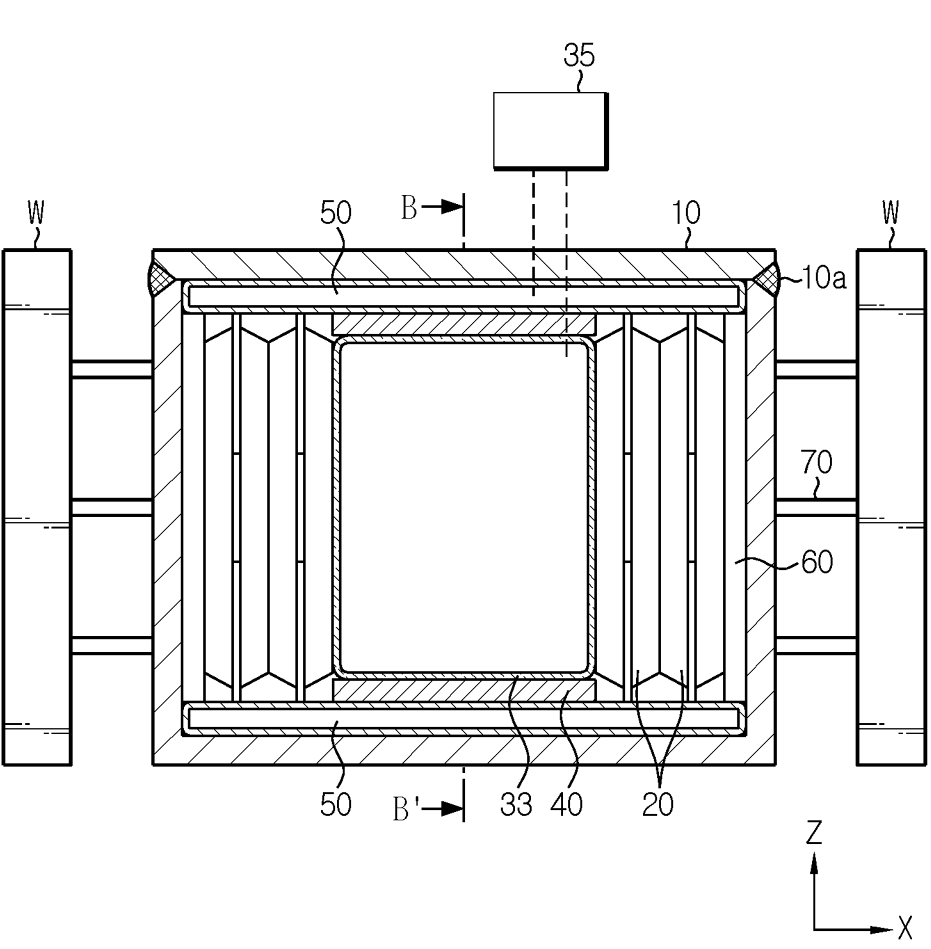
FIGS. 7 and 8 are views illustrating a fatigue failure verification device according to Third Embodiment of the present disclosure.
Figure 8:
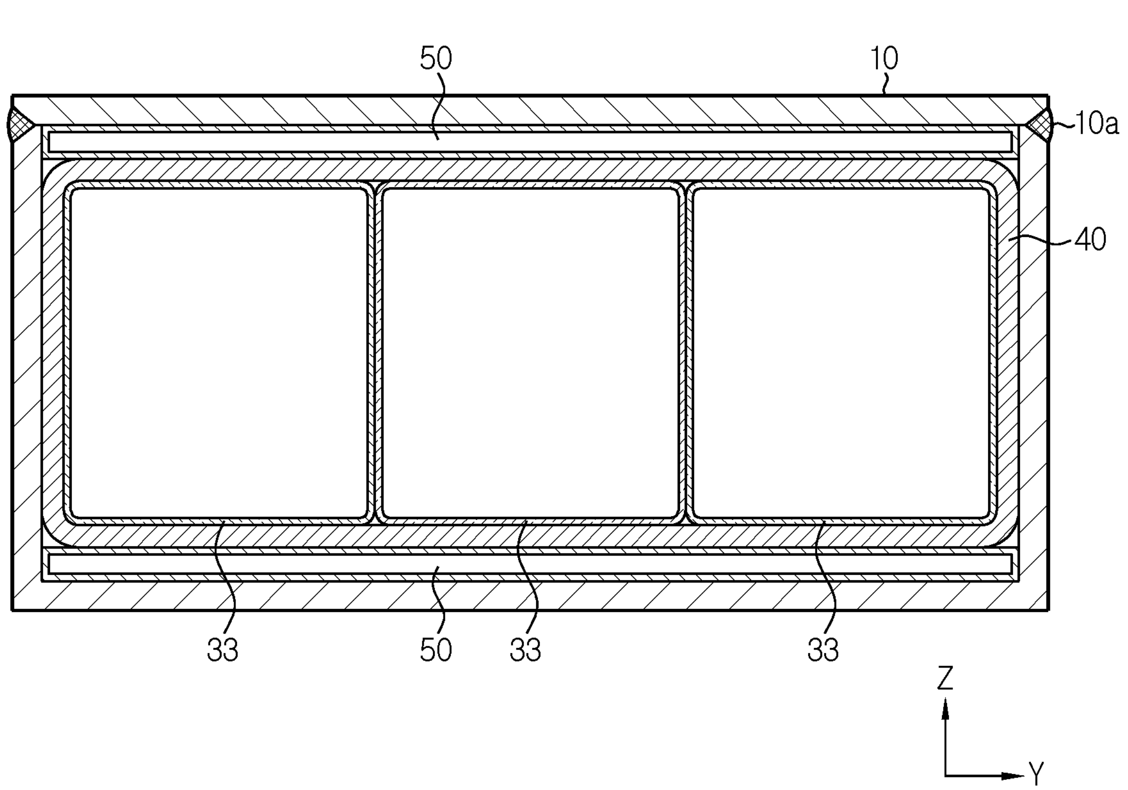
Figure 9:
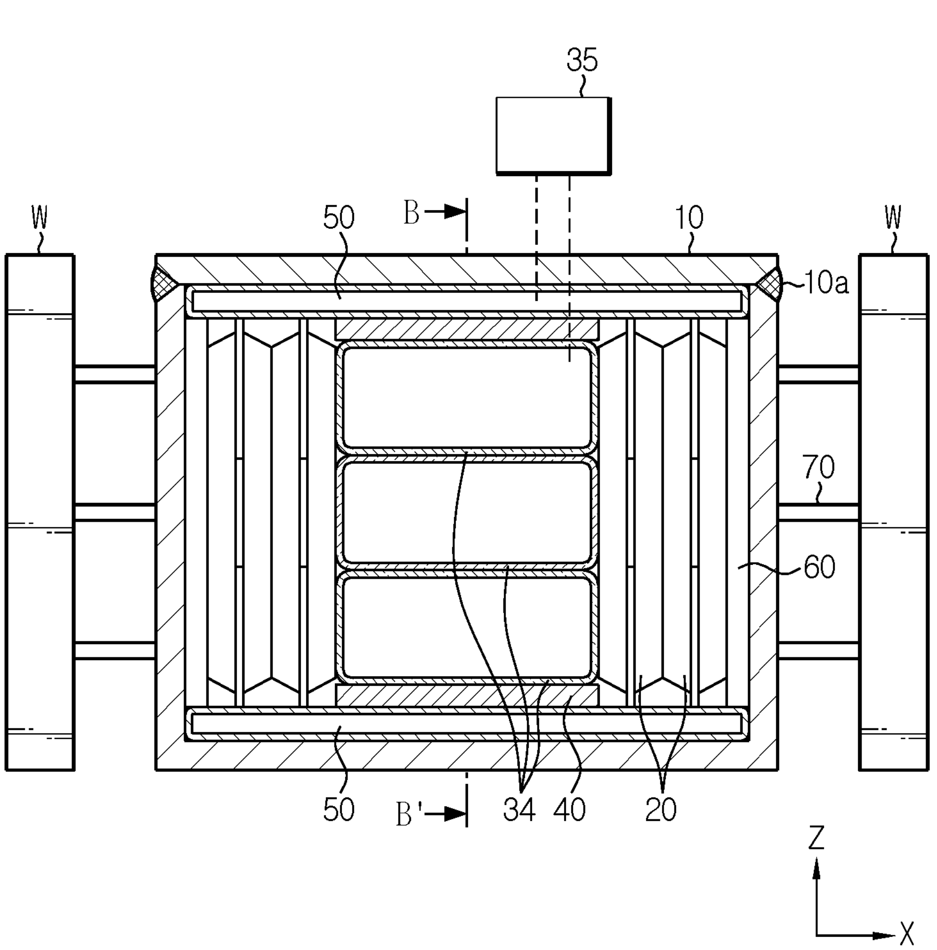
FIGS. 9 and 10 are views illustrating a fatigue failure verification device according to Fourth Embodiment of the present disclosure.
Figure 10:
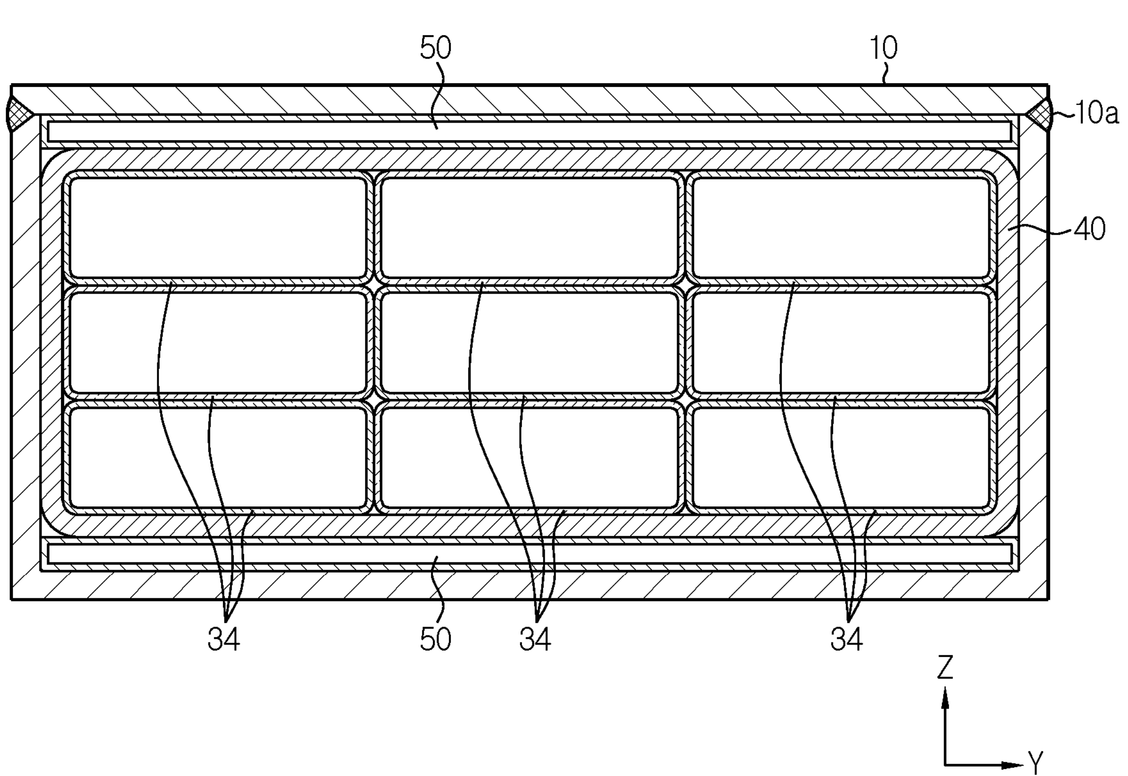

When compared to the above embodiment, a fatigue failure verification device according to Second Embodiment of the present disclosure illustrated in FIGS. 5 and 6, a fatigue failure verification device according to Third Embodiment of the present disclosure illustrated in FIGS. 7 and 8, and a fatigue failure verification device according to Fourth Embodiment of the present disclosure illustrated in FIGS. 9 and 10 are different in the number of the main flexible tubes 32, 33, 34 and an arrangement in the main flexible tube frame 40, but other elements are substantially the same and effects thereof are also substantially very similar.

Accordingly, in describing the fatigue failure verification devices according to Second through Fourth Embodiments of the present disclosure, the number and arrangement of the main flexible tubes 32, 33, 34 will be mainly described, and the same description as that made in First Embodiment will not be provided.

First, referring to FIGS. 5 and 6, the fatigue failure verification device according to Second Embodiment of the present disclosure includes a plurality of main flexible tubes 32, and the plurality of main flexible tubes 32 are staked in the width direction (direction parallel to the Z-axis) of the battery cell 20 in the main flexible tube frame 40. In this case, the pump 35 may individually control the amount of a fluid supplied to each main flexible tube 32. Accordingly, the plurality of main flexible tubes 32 may press with different forces according to positions in the width direction of the battery cell 20. Actually, the degree of volume expansion due to swelling may vary according to positions in the width direction of the battery cell 20 during swelling of the battery cell 20. Because the fatigue failure verification device according to Second Embodiment of the present disclosure may allow the plurality of main flexible tubes 32 to press the battery cell 20 with different forces, an environment similar to an actual swelling environment may be created.

Next, referring to FIGS. 7 and 8, the fatigue failure verification device according to Third Embodiment of the present disclosure includes a plurality of main flexible tubes 33, and the plurality of main flexible tubes 33 are stacked in the longitudinal direction (direction parallel to the Y-axis) of the battery cell 20 in the main flexible tube frame 40. In this case, the pump 35 may individually control the amount of a fluid supplied to each main flexible tube 33. Accordingly, the plurality of main flexible tubes 33 may press with different forces according to positions in the longitudinal direction of the battery cell 20. Actually, the degree of volume expansion due to swelling may vary according to positions in the longitudinal direction of the battery cell 20 during swelling of the battery cell 20. Because the fatigue failure verification device according to Third Embodiment of the present disclosure may allow the plurality of main flexible tubes 33 to press the battery cell 20 with different forces, an environment similar to an actual swelling environment may be created.

Next, referring to FIGS. 9 and 10, the fatigue failure verification device according to Fourth Embodiment of the present disclosure includes a plurality of main flexible tubes 34, and the plurality of main flexible tubes 34 are stacked in the longitudinal direction and the width direction of the battery cell 20 in the main flexible tube frame 40. In this case, the pump 35 may individually control the amount of a fluid supplied to each main flexible tube 34. Accordingly, the plurality of main flexible tubes 34 may press with different forces according to positions in the longitudinal direction and the width direction of the battery cell 20. Actually, the degree of volume expansion due to swelling may vary according to positions in the longitudinal direction and the width direction of the battery cell 20 during swelling of the battery cell 20. Because the fatigue failure verification device according to Fourth Embodiment of the present disclosure may allow the plurality of main flexible tubes 34 to press the battery cell 20 with different forces, an environment similar to an actual swelling environment may be created.

Although the embodiments of the present disclosure have been illustrated and described above, the present disclosure is not limited to the above-described specific embodiments. Various modified embodiments may be made by one of ordinary skill in the art without departing from the scope of the present disclosure as claimed in the claims.

What is claimed is:

1. A fatigue failure verification device comprising:

a module housing comprising a welding portion;

a cell stack comprising a plurality of battery cells accommodated in the module housing;

at least one main flexible tube located in a central portion of the cell stack in a stack direction of the cell stack;

a main flexible tube frame in which the at least one main flexible tube is accommodated, the main flexible tube frame comprising a pair of opening portions formed on opposite sides so that the at least one main flexible tube faces the plurality of battery cells; and a pump configured to adjust a pressure applied by the at least one main flexible tube to the plurality of battery cells by supplying a fluid to the at least one main flexible tube, wherein the main flexible tube frame surrounds an outer periphery of the at least one main flexible tube so as to limit a volume expansion direction of the at least one main flexible tube to only the stack direction of the cell stack, wherein the at least one main flexible tube is housed in surface contact with an inner peripheral surface of the main flexible tube frame along a length of the inner peripheral surface of the main flexible tube frame in the stack direction of the cell stack, and wherein the inner peripheral surface of the main flexible tube frame is a planar surface that extends continuously from one of the pair of opening portions to another of the pair of opening portions in the stack direction of the cell stack.

2. The fatigue failure verification device of claim 1, further comprising a pair of sub-flexible tubes respectively located between an upper plate of the module housing and the cell stack and between the upper plate of the module housing and the main flexible tube frame, and between a lower plate of the module housing and the cell stack and between the lower plate of the module housing and the main flexible tube frame.

3. The fatigue failure verification device of claim 2, wherein the pump is configured to individually control an amount of the fluid supplied to the at least one main flexible tube and the pair of sub-flexible tubes.

4. The fatigue failure verification device of claim 1, wherein the fatigue failure verification device is located between a pair of support walls, and wherein the fatigue failure verification device further comprises a plurality of displacement sensors respectively located between a side of the module housing in a longitudinal direction of the module housing and one of the pair of support walls and between another side of the module housing in the longitudinal direction of the module housing and another of the pair of support walls.

5. The fatigue failure verification device of claim 1, further comprising a pair of buffer pads respectively provided on opposite outermost sides of the cell stack in the stack direction of the cell stack.

6. The fatigue failure verification device of claim 1, wherein a plurality of main flexible tubes are provided, and wherein the plurality of main flexible tubes are stacked in a width direction of the plurality of battery cells in the main flexible tube frame.

7. The fatigue failure verification device of claim 6, wherein the pump is configured to individually control an amount of the fluid supplied to the plurality of main flexible tubes.

8. The fatigue failure verification device of claim 7, further comprising a pair of sub-flexible tubes respectively located between an upper plate and a lower plate of the module housing and the cell stack, and between the upper plate and the lower plate of the module housing and the main flexible tube frame, wherein the pump is configured to individually control an amount of the fluid supplied to the plurality of main flexible tubes and the pair of sub-flexible tubes.

9. The fatigue failure verification device of claim 1, wherein a plurality of main flexible tubes are provided, and wherein the plurality of main flexible tubes are stacked in a longitudinal direction of the plurality of battery cells in the main flexible tube frame.

10. The fatigue failure verification device of claim 9, wherein the pump is configured to individually control an amount of the fluid supplied to the plurality of main flexible tubes.

11. The fatigue failure verification device of claim 10, further comprising a pair of sub-flexible tubes respectively located between an upper plate and a lower plate of the module housing and the cell stack, and between the upper plate and the lower plate of the module housing and the main flexible tube frame, wherein the pump is configured to individually control an amount of the fluid supplied to the plurality of main flexible tubes and the pair of sub-flexible tubes.

12. The fatigue failure verification device of claim 1, wherein a plurality of main flexible tubes are provided, and wherein the plurality of main flexible tubes are stacked in a width direction and a longitudinal direction of the plurality of battery cells in the main flexible tube frame.

13. The fatigue failure verification device of claim 12, wherein the pump is configured to individually control an amount of the fluid supplied to the plurality of main flexible tubes.

14. The fatigue failure verification device of claim 13, further comprising a pair of sub-flexible tubes respectively located between an upper plate and a lower plate of the module housing and the cell stack, and between the upper plate and the lower plate of the module housing and the main flexible tube frame, wherein the pump is configured to individually control an amount of the fluid supplied to the plurality of main flexible tubes and the pair of sub-flexible tubes.

15. The fatigue failure verification device of claim 1, wherein the main flexible tube frame includes an outer peripheral surface that is in surface contact with an inner peripheral surface of the module housing along a length of the outer peripheral surface of the main flexible tube frame in the stack direction of the cell stack.

* * * * *